United States Patent [19]
Van der Flass et al.

[11] Patent Number: 5,932,520
[45] Date of Patent: Aug. 3, 1999

[54] USE OF PYRROLE COMPOUNDS AS ANTIFOULING AGENTS

[75] Inventors: Mark Arthur Josepha Van der Flass, Herselt, Belgium; Lantz Stephen Crawley, Pennington, N.J.

[73] Assignee: American Cyanamid Company, Madison, N.J.

[21] Appl. No.: 08/448,240

[22] Filed: May 23, 1995

[51] Int. Cl.$^6$ .............................. A01N 43/36; A01N 43/40
[52] U.S. Cl. .................. 504/156; 514/277; 514/338; 514/354; 514/422; 514/423; 514/424; 514/425; 514/426; 514/427; 514/428; 514/429
[58] Field of Search ................................. 514/422, 423, 514/424, 338, 354, 277, 425, 426, 427, 428, 429; 504/156

[56] References Cited

U.S. PATENT DOCUMENTS 4,737,510  4/1988  Rinehart, Jr. .............................. 514/388
5,310,938  5/1994  Brown et al. ............................. 548/557
5,328,928  7/1994  Addor et al. ............................. 514/423

OTHER PUBLICATIONS

Personne et al, A Simple Bioassay with Artemia Larvae to Determine the Acute Toxicity of Antifouling Paints, Water Research, 23 (7) pp. 893–7 (1989).

*Primary Examiner*—Allen J. Robinson
*Attorney, Agent, or Firm*—Gregory M. Hill

[57] ABSTRACT

There is provided a method for controlling or combatting the attachment of a fouling organism to an underwater surface which comprises contacting said organism with an antifouling-effective amount of a 2-arylpyrrole compound. A method for protecting aquatic structures against fouling by a marine or freshwater fouling organism and antifoulant compositions therefor are also provided.

9 Claims, No Drawings

USE OF PYRROLE COMPOUNDS AS ANTIFOULING AGENTS

BACKGROUND OF THE INVENTION

The ever recurring growth of fouling organisms on underwater structures such as ships, docks, piers, pilings, fishnets, heat exchangers, dams, piping structures, intake screens, cooling towers and the like is a costly and hazardous problem in both marine and freshwater endeavors. The presence of fouling organisms such as barnacles, zebra mussels, algae, diatoms, hydroids, bryozoa, ascidians, tubeworms, Asiatic clams and the like can weigh down aquatic structures, hamper their hydrodynamics, reduce operating efficiency, increase susceptibility to corrosion, cause degradation and structural fractures, block or hamper water flow and water exchange and the like. A common method of controlling the presence or attachment of fouling organisms is to coat or permeate the underwater structure with a composition which comprises a toxic metal-containing compound such as tri-n-butyl tin or cuprous oxide. Although said compositions are somewhat efficacious antifoulants, they degrade slowly in aquatic environments and are, therefore, ecologically harmful.

Arylpyrrole compounds and N-acylated arylpyrrole compounds are known to be effective insecticidal and endectocidal agents useful in crop protection and animal health; said pyrrole compounds are described in U.S. Pat. Nos. 5,310,938 and 5,328,928, respectively.

It is an object of this invention to provide an environmentally and ecologically sound method of combatting or controlling marine and freshwater fouling organisms without the use of toxic metal-containing compounds.

It is another object of this invention to provide an effective method for protecting aquatic structures against fouling by marine or freshwater fouling organisms.

It is a further object of this invention to provide antifoulant compositions which comprise 2-arylpyrrole and acylated 2-arylpyrrole compounds as the active agents.

It is a feature of this invention that the antifouling methods and compositions are free of heavy metal complexes and toxic metal-containing compounds.

These and other features and objects of the invention will become more apparent from the detailed description set forth hereinbelow.

SUMMARY OF THE INVENTION

The present invention provides a method for controlling or combatting a marine or freshwater fouling organism which comprises contacting said organism with an antifouling-effective amount of a 2-arylpyrrole compound of formula I

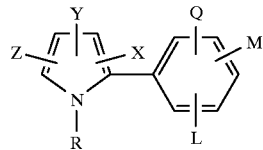

wherein
X is halogen, CN, $NO_2$ or $S(O)_nR_1$;
Y is hydrogen, halogen or $S(O)_nR_1$;
Z is halogen, $C_1$–$C_4$haloalkyl or $S(O)_nR_1$;
n is an integer of 0, 1 or 2;
$R_1$ is $C_1$–$C_4$haloalkyl;
L is hydrogen or halogen;
M and Q are each independently hydrogen, halogen, $C_1$–$C_4$ alkyl, $C_1$–$C_4$haloalkyl, $C_1$–$C_4$alkoxy, $C_1$–$C_4$alkylthio, $C_1$–$C_4$alkylsulfinyl, $C_1$–$C_4$alkylsulfonyl, CN, $NO_2$, $R_2CO$ or $NR_3R_4$, or when M and Q are on adjacent positions and are taken together with the carbon atoms to which they are attached MQ represents the structure —$OCH_2O$—, —$OCF_2O$—, or —CH=CH—CH=CH—;
R is hydrogen, $C_1$–$C_4$alkoxyalkyl, $C_1$–$C_4$alkythioalkyl or $R_6CO$;
$R_2$ is $C_1$–$C_4$alkyl, $C_1$–$C_4$haloalkyl, $C_1$–$C_4$alkoxy or $NR_3R_4$;
$R_3$ is hydrogen or $C_1$–$C_4$alkyl;
$R_4$ is hydrogen, $C_1$–$C_4$alkyl or $R_5CO$;
$R_5$ is hydrogen or $C_1$–$C_4$alkyl; and
$R_6$ is $C_1$–$C_4$alkyl, $C_1$–$C_4$haloalkyl, $C_1$–$C_4$alkoxy, $C_2$–$C_6$alkenyloxy, $C1$–$C_4$haloalkoxy, phenyl optionally substituted with one to three $C_1$–$C_4$alkyl groups, benzyl, phenoxy, benzyloxy, $C_1$–$C_4$alkylcarbonyloxy, $C_3$–$C_6$cycloalkyl, naphthyl, pyridyl, thienyl or furanyl.

The present invention also provides a method for the protection of aquatic structures against fouling by a marine or freshwater fouling organism and an antifoulant composition suitable for use therefor.

DETAILED DESCRIPTION OF THE INVENTION

Controlling or combatting fouling organisms in aquatic environments without harming beneficial species or threatening the ecological balance of said environment is a continuing scientific challenge. It has now been found that 2-arylpyrrole compounds having a hydrogen or a hydrolyticly labile group on the pyrrole ring nitrogen atom are particularly effective as antifouling agents. Preferably, the 2-arylpyrroles useful for combatting and controlling marine and freshwater fouling organisms are those compounds having the structure of formula I

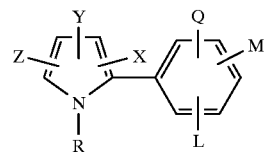

wherein
X is halogen, CN, $NO_2$ or $S(O)_nR_1$;
Y is hydrogen, halogen or $S(O)_nR_1$;
Z is halogen, $C_1$–$C_4$haloalkyl or $S(O)_nR_1$;
n is an integer of 0, 1 or 2;
$R_1$ is $C_1$–$C_4$haloalkyl;
L is hydrogen or halogen;
M and Q are each independently hydrogen, halogen, $C_1$–$C_4$ alkyl, $C_1$–$C_4$haloalkyl, $C_1$–$C_4$alkoxy, $C_1$–$C_4$alkylthio, $C_1$–$C_4$alkylsulfinyl, $C_1$–$C_4$alkylsulfonyl, CN, $NO_2$, $R_2CO$ or $NR_3R_4$, or when M and Q are on adjacent positions and are taken together with the carbon atoms to which they are attached MQ represents the structure —$OCH_2O$—, —$OCF_2O$—, or —CH=CH-CH=CH—;
R is hydrogen, $C_1$–$C_4$alkoxyalkyl, $C_1$–$C_4$alkythioalkyl or $R_6CO$;

$R_2$ is $C_1$–$C_4$alkyl, $C_1$–$C_4$haloalkyl, $C_1$–$C_4$alkoxy or $NR_3R_4$;

$R_3$ is hydrogen or $C_1$–$C_4$alkyl;

$R_4$ is hydrogen, $C_1$–$C_4$alkyl or $R_5CO$;

$R_5$ is hydrogen or $C_1$–$C_4$alkyl; and $R_6$ is $C_1$–$C_4$alkyl, $C_1$–$C_4$haloalkyl, $C_1$–$C_4$alkoxy, $C_2$–$C_6$ alkenyloxy, C1–$C_4$haloalkoxy, phenyl optionally substituted with one to three $C_1$–$C_4$alkyl groups, benzyl, phenoxy, benzyloxy, $C_1$–$C_4$alkylcarbonyloxy, $C_3$–$C_6$ cycloalkyl, naphthyl, pyridyl, thienyl or furanyl.

More preferred antifoulant agents suitable for use in the methods and composition of the invention are those 2-arylpyrrole compounds of formula I wherein R is hydrogen, L is hydrogen or halogen and M and Q are each independently hydrogen, halogen or $C_1$–$C_4$haloalkyl.

In the specification and claims the term halogen designates Cl, Br, I or F and the term haloalkyl designates any alkyl group $C_nH_{2n+1}$ having from 1 halogen atom to 2n+1 halogen atoms wherein the halogen atoms are the same or different.

Among the 2-arylpyrrole compounds suitable for use in the methods and composition of the invention are:

4,5-dichloro-2-(α,α,α-trifluoro-p-tolyl)pyrrole-3-carbonitrile;

4-bromo-5-chloro-2-(p-chlorophenyl)pyrrole-3-carbonitrile;

4-bromo-2-(p-chlorophenyl)-5-(trifluoromethyl)pyrrole-3-carbonitrile;

3,4-dichloro-2-(3,4-dichlorophenyl)pyrrole-5-carbonitrile;

4-chloro-2-(p-chlorophenyl)-5-(trifluoromethyl)pyrrole-3-carbonitrile;

4,5-dibromo-2-(p-chlorophenyl)-3-(trifluoromethylsulfonyl)pyrrole;

4-bromo-2-(3,5-dichlorophenyl)-5-(trifluoromethyl)pyrrole-3-carbonitrile;

2-(p-chlorophenyl)-5-(trifluoromethyl)-4-(trifluoromethylthio)pyrrole-3-carbonitrile;

4-bromo-2-(2,3,4-trichlorophenyl)-5-(trifluoromethyl)pyrrole-3-carbonitrile;

4-bromo-2-(2,3,5-trichlorophenyl)-5-(trifluoromethyl)pyrrole-3-carbonitrile;

4-bromo-2-(p-chlorophenyl)-5-(α,α,β,β-tetrafluoroethylthio)pyrrole-3-carbonitrile;

4-bromo-2-(m-fluorophenyl)-5-(trifluoromethyl)pyrrole-3-carbonitrile;

2-(3,5-dichlorophenyl)-5-(trifluoromethyl)-4-(trifluoromethylthio)pyrrole-3-carbonitrile; and 4-bromo-2-(p-chlorophenyl)-5-[(β-bromo-β,α,α-trifluoro)ethylthio]pyrrole-3-carbonitrile.

Said formula I arylpyrrole compounds and methods to prepare same are described in U.S. Pat. Nos. 5,310,938 and 5,328,928, herein incorporated by reference.

A fouling organism which may be combatted or controlled by the method of the invention can be any marine or freshwater organism which can attach to an inner or outer surface of a structure which is submerged or in continual contact with water. Exemplary organisms include algae, including members of the phyla Chlorophyta and Phaeophyta, microbes, tunicates, including members of the class Ascidiancea, such as *Ciona intestinalis, Diplosoma listerianium*, and *Botryllus sclosseri*, members of the class Hydrozoa, including *Clava squamata, Hydractinia echinata, Obelia geniculata*, and *Tubularia larnyx*, bivalves, including *Mytilus edulis, Crassostrea virginica, Ostrea edulis, Ostrea chilensia*, and *Lasaea rubra*, bryozoans, including *Ectra pilosa, Bugula neritinia*, and *Bowerbankia gracilis*, polychaete worms, including *Hydroides norvegica*, sponges and members of the class Cirripedia (barnacles), such as *Balanus amphitrite, Lepas anatifera, Balanus balanus, Balanus balanoides, Balanus hameri, Balanus crenatus, Balanus improvisus, Balanus galeatus*, and *Balanus eburneus*. Organisms of the genus Balanus are frequent foulers of aquatic structures. Specific fouling organisms to which this invention is especially directed include barnacles, zebra mussels, algae, diatoms, hydroids, bryozoa, ascidians, tube worms and Asiatic clams.

Among the aquatic structures which may be protected by the method of invention are any submerged or partially submerged structure, either mobile or stationary, such as a fishnet, boat, ship, piling, pier, cooling tower, pipeline, standpipe, heat exchanger, dam, intake screen or the like.

In actual practice the antifouling 2-arylpyrrole compound may be brought into contact with a fouling organism by: a) coating the aquatic structure to be protected with an antifouling-effective amount of said 2-arylpyrrole compound such that the antifouling compound is released into the aquatic environment immediately adjacent the external surface of said structure, b) including an antifouling-effective amount of the 2-arylpyrrole compound within material formed into an aquatic structure which then releases said compound, c) releasing an antifouling-effective amount of said compound directly into the aquatic environment surrounding the structure to be protected, or d) any other method wherein the 2-arylpyrrole compound comes in contact with the fouling organism.

The amount of 2-arylpyrrole compound to be used in the method of invention will vary according to the specific compound used, the identity of the fouling organism to be controlled, degree of infestation of the surrounding aquatic environment, the water temperature, the mode of contact and the like.

Compositions of the invention comprise an aquatically acceptable inert carrier and an antifouling-effective amount of a 2-arylpyrrole compound, preferably a compound of formula I. For application onto structural surfaces, preferred compositions of the invention include a film-forming component such as a polymer resin solution. Exemplary polymer resins include unsaturated polyester resins formed from: a) unsaturated acids or anhydrides, such as maleic anhydride, fumaric acid, itaconic acid and the like; b) saturated acids or anhydrides, such as phthalic anhydride, isophthalic anhydride, terephthalic anhydride, tetrahydrophthalic anhydride, tetrahalophthalic anhydride, chlorendic acid, adipic acid, subacic acid, and the like; c) glycols, such as ethylene glycol, 1,2 propylene glycol, dibromoneopentyl glycol, and the like; or d) vinyl monomers, such as styrene, vinyl toluene, chlorostyrene, bromostyrene, methylmethacrylate, ethylene glycol dimethacrylate and the like. Other suitable resins include vinyl ester-, vinyl acetate-, and vinyl chloride-based resins, elastomeric components, vulcanized rubbers, and urethane-based resins.

In order to present a clearer understanding of the invention, specific examples thereof are set forth below. These examples are merely illustrative and are not to be understood as limiting the scope and underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Evaluation Of Marine Antifouling Activity Of Test Compounds

The crustaceous marine animal *Artemia salina* is used as a model organism for other marine animal foulers (e.g.

barnacles) in this laboratory assay. Test compounds are dissolved in dimethylsulfoxide at a concentration of 4,000 ppm, diluted to a concentration of 200 ppm with water and further diluted with Probst artificial seawater to a concentration of 10 ppm. Approximately 30 *Artemia salina* instar II larvae are incubated in microwell plates in 2 ml of Probst artificial seawater containing 10 ppm of the test compound. Survival of the organism is evaluated after 24 hours, and test compounds are rated according to the scale shown below. Test results are shown in Table I.

RATING SCALE

| Rating | Definition |
| --- | --- |
| 1 | No activity, 0%–<20% mortality |
| 2 | Toxic effect; 20%–80% mortality |
| 3 | Completely active, >80% mortality |

TABLE I

| Test Compound | Art[1] |
| --- | --- |
| 4,5-dichloro-2-(α,α,α-trifluoro-p-tolyl)pyrrole-3-carbonitrile; | 3 |
| 4-bromo-5-chloro-2-(p-chlorophenyl)pyrrole-3-carbonitrile; | 3 |
| 4-bromo-2-(p-chlorophenyl)-5-(trifluoromethyl)-pyrrole-3-carbonitrile; | 3 |
| 3,4-dichloro-2-(3,4-dichlorophenyl)pyrrole-5-carbonitrile; | 3 |
| 4-chloro-2-(p-chlorophenyl)-5-(trifluoromethyl)-pyrrole-3-carbonitrile; | 3 |
| 4,5-dibromo-2-(p-chlorophenyl)-3-(trifluoromethylsulfonyl)pyrrole; | 3 |
| 4-bromo-2-(3,5-dichlorophenyl)-5-(trifluoromethyl)pyrrole-3-carbonitrile; | 3 |
| 2-(p-chlorophenyl)-5-(trifluoromethyl)-4-(trifluoromethylthio)pyrrole-3-carbonitrile; | 3 |
| 4-bromo-2-(2,3,4-trichlorophenyl)-5-(trifluoromethyl)pyrrole-3-carbonitrile; | 3 |
| 4-bromo-2-(2,3,5-trichlorophenyl)-5-(trifluoromethyl)pyrrole-3-carbonitrile; | 3 |
| 4-bromo-2-(p-chlorophenyl)-5-(α,α,β,β-tetrafluoroethylthio)pyrrole-3-carbonitrile; | 3 |
| 4-bromo-2-(m-fluorophenyl)-5-(trifluoromethyl)-pyrrole-3-carbonitrile; | 3 |
| 2-(3,5-dichlorophenyl)-5-(trifluoromethyl)-4-(trifluoromethylthio)pyrrole-3-carbonitrile; | 3 |
| 4-bromo-2-(p-chlorophenyl)-5-[(β-bromo-β,α,α-trifluoro)ethylthio]pyrrole-3-carbonitrile. | 3 |

[1]Artemia

EXAMPLE 2

Evaluation Of Freshwater Antifouling Activity Of Test Compounds

The test compound is mechanically dispersed in 1L of water to give a stock solution having a concentration of 254 mg/L of active ingredient. This stock solution is subsequently diluted to give further test concentrations. The water used is a 1:1 mixture of well water and distilled water. Ten adult zebra mussels of approximately equal biomass are placed in a 2L white polypropylene bucket containing 90 mL of test solution. All test concentrations are replicated and two controls are used.

Mortality is recorded at 24 hour intervals. Mortality is recorded if the mussel fails to close its valves upon gently prodding as compared to control.

The test compound used is 4-bromo-2-(p-chlorophenyl)-5-(trifluoromethyl)pyrrole-3-carbonitrile.

The daily mortality at each concentration is shown in Table II.

TABLE II

| Concentration | Mortality | | | | Total after |
| --- | --- | --- | --- | --- | --- |
| (mg/L) | 24h | 48h | 72h | 96h | 96h |
| 254 | 10 10 | — — | — — | — — | 20 |
| 25.4 | 10 10 | — — | — — | — — | 20 |
| 2.54 | 10 10 | — — | — — | — — | 20 |
| 0.254 | 1 1 | 3 2 | 4 4 | 2 2 | 19 |
| 0.025 | 0 0 | 1 0 | 3 2 | 1 2 | 9 |
| Control | 0 0 | 0 0 | 0 0 | 0 0 | 0 |

What is claimed is:

1. A method for controlling or combatting the attachment of a fouling organism selected from the group consisting of barnacles, zebra mussels, algae, diatoms, hydroids, bryozoa, ascidians, tubeworms and Asiatic clams to an underwater surface which comprises contacting said organism with an antifouling-effective amount of a compound of formula I

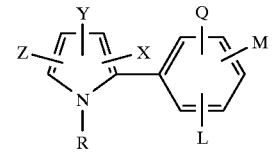

wherein

X is halogen, CN, $NO_2$ or $S(O)_nR_1$;

Y is hydrogen, halogen or $S(O)_nR_1$;

Z is halogen, $C_1$–$C_4$haloalkyl or $S(O)_nR_1$;

n is an integer of 0, 1 or 2;

$R_1$ is $C_1$–$C_4$haloalkyl;

L is hydrogen or halogen;

M and Q are each independently hydrogen, halogen, $C_1$–$C_4$ alkyl, $C_1$–$C_4$haloalkyl, $C_1$–$C_4$alkoxy, $C_1$–$C_4$alkylthio, $C_1$–$C_4$alkylsulfinyl, $C_1$–$C_4$alkylsulfonyl, CN, $NO_2$, $R_2CO$ or $NR_3R_4$, or when M and Q are on adjacent positions and are taken together with the carbon atoms to which they are attached MQ represents the structure —$OCH_2O$—, —$OCF_2O$—, or —CH=CH-CH=CH—;

R is hydrogen, $C_1$–$C_4$alkoxyalkyl, $C_1$–$C_4$alkythioalkyl or $R_6CO$;

$R_2$ is $C_1$–$C_4$alkyl, $C_1$–$C_4$haloalkyl, $C_1$–$C_4$alkoxy or $NR_3R_4$;

$R_3$ is hydrogen or $C_1$–$C_4$alkyl;

$R_4$ is hydrogen, $C_1$–$C_4$alkyl or $R_5CO$;

$R_5$ is hydrogen or $C_1$–$C_4$alkyl; and $R_6$ is $C_1$–$C_4$alkyl, $C_1$–$C_4$haloalkyl, $C_1$–$C_4$alkoxy, $C_2$–$C_6$ alkenyloxy, $C_1$–$C_4$haloalkoxy, phenyl optionally substituted with one to three $C_1$–$C_4$alkyl groups, benzyl, phenoxy, benzyloxy, $C_1$–$C_4$alkylcarbonyloxy, $C_3$–$C_6$ cycloalkyl, naphthyl, pyridyl, thienyl or furanyl.

2. The method according to claim 1 wherein R is hydrogen.

3. The method according to claim 1 wherein L is hydrogen or halogen and M and Q are each independently hydrogen, halogen or $C_1$–$C_4$haloalkyl.

4. The method according to claim 2 wherein the formula I compound is selected from the group consisting of 4,5-dichloro-2-(α,α,α-trifluoro-p-tolyl)pyrrole-3-carbonitrile;

4-bromo-5-chloro-2-(p-chlorophenyl)pyrrole-3-carbonitrile;

4-bromo-2-(p-chlorophenyl)-5-(trifluoromethyl)pyrrole-3-carbonitrile;

3,4-dichloro-2-(3,4-dichlorophenyl)pyrrole-5-carbonitrile;

4-chloro-2-(p-chlorophenyl)-5-(trifluoromethyl)pyrrole-3-carbonitrile;

4,5-dibromo-2-(p-chlorophenyl)-3-(trifluoromethylsulfonyl)pyrrole;

4-bromo-2-(3,5-dichlorophenyl)-5-(trifluoromethyl)pyrrole-3-carbonitrile;

2-(p-chlorophenyl)-5-(trifluoromethyl)-4-(trifluoromethylthio)pyrrole-3-carbonitrile;

4-bromo-2-(2,3,4-trichlorophenyl)-5-(trifluoromethyl)-pyrrole-3-carbonitrile;

4-bromo-2-(2,3,5-trichlorophenyl)-5-(trifluoromethyl)-pyrrole-3-carbonitrile;

4-bromo-2-(p-chlorophenyl)-5-($\alpha,\alpha,\beta,\beta$-tetrafluoroethylthio)pyrrole-3-carbonitrile;

4-bromo-2-(m-fluorophenyl)-5-(trifluoromethyl)pyrrole-3-carbonitrile;

2-(3,5-dichlorophenyl)-5-(trifluoromethyl)-4-(trifluoromethylthio)pyrrole-3-carbonitrile; and 4-bromo-2-(p-chlorophenyl)-5-[($\beta$-bromo-$\beta,\alpha,\alpha$-trifluoro)-ethylthio]pyrrole-3-carbonitrile.

5. A method for protecting an aquatic structure against fouling by a marine or freshwater fouling organism selected from the group consisting of barnacles, zebra mussels, algae, diatoms, hydroids, bryozoa, ascidians, tubeworms and Asiatic clams which comprises applying onto or permeating into said structure an antifouling-effective amount of a compound of formula I

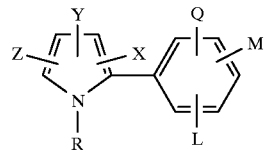

wherein

X is halogen, CN, $NO_2$ or $S(O)_nR_1$;

Y is hydrogen, halogen or $S(O)_nR_1$;

Z is halogen, $C_1$–$C_4$haloalkyl or $S(O)_nR_1$;

n is an integer of 0, 1 or 2;

$R_1$ is $C_1$–$C_4$haloalkyl;

L is hydrogen or halogen;

M and Q are each independently hydrogen, halogen, $C_1$–$C_4$ alkyl, $C_1$–$C_4$haloalkyl, $C_1$–$C_4$alkoxy, $C_1$–$C_4$alkylthio, $C_1$–$C_4$alkylsulfinyl, $C_1$–$C_4$alkylsulfonyl, CN, $NO_2$, $R_2CO$ or $NR_3R_4$, or when M and Q are on adjacent positions and are taken together with the carbon atoms to which they are attached MQ represents the structure —$OCH_2O$—, —$OCF_2O$—, or —CH=CH—CH=CH—;

R is hydrogen, $C_1$–$C_4$alkoxyalkyl, $C_1$–$C_4$alkythioalkyl or $R_6CO$;

$R_2$ is $C_1$–$C_4$alkyl, $C_1$–$C_4$haloalkyl, $C_1$–$C_4$alkoxy or $NR_3R_4$;

$R_3$ is hydrogen or $C_1$–$C_4$alkyl;

$R_4$ is hydrogen, $C_1$–$C_4$alkyl or $R_5CO$;

$R_5$ is hydrogen or $C_1$–$C_4$alkyl; and $R_6$ is $C_1$–$C_4$alkyl, $C_1$–$C_4$haloalkyl, $C_1$–$C_4$alkoxy, $C_2$–C6 alkenyloxy, C1–$C_4$haloalkoxy, phenyl optionally substituted with one to three $C_1$–$C_4$alkyl groups, benzyl, phenoxy, benzyloxy, $C_1$–$C_4$alkylcarbonyloxy, $C_3$–$C_6$ cycloalkyl, naphthyl, pyridyl, thienyl or furanyl.

6. The method according to claim 5 wherein R is hydrogen.

7. The method according to claim 5 wherein L is hydrogen or halogen and M and Q are each independently hydrogen, halogen or $C_1$–$C_4$haloalkyl.

8. The method according to claim 5 wherein the aquatic structure is a fishnet, boat, ship, piling, pier, intake screen, cooling tower, pipeline or standpipe.

9. The method according to claim 6 wherein the formula I compound is selected from the group consisting of 4,5-dichloro-2-($\alpha,\alpha,\alpha$-trifluoro-p-tolyl)pyrrole-3-carbonitrile;

4-bromo-5-chloro-2-(p-chlorophenyl)pyrrole-3-carbonitrile;

4-bromo-2-(p-chlorophenyl)-5-(trifluoromethyl)pyrrole-3-carbonitrile;

3,4-dichloro-2-(3,4-dichlorophenyl)pyrrole-5-carbonitrile;

4-chloro-2-(p-chlorophenyl)-5-(trifluoromethyl)pyrrole-3-carbonitrile;

4,5-dibromo-2-(p-chlorophenyl)-3-(trifluoromethylsulfonyl)pyrrole;

4-bromo-2-(3,5-dichlorophenyl)-5-(trifluoromethyl)pyrrole-3-carbonitrile;

2-(p-chlorophenyl)-5-(trifluoromethyl)-4-(trifluoromethylthio)pyrrole-3-carbonitrile;

4-bromo-2-(2,3,4-trichlorophenyl)-5-(trifluoromethyl)-pyrrole-3-carbonitrile;

4-bromo-2-(2,3,5-trichlorophenyl)-5-(trifluoromethyl)-pyrrole-3-carbonitrile;

4-bromo-2-(p-chlorophenyl)-5-($\alpha,\alpha,\beta,\beta$-tetrafluoroethylthio)pyrrole-3-carbonitrile;

4-bromo-2-(m-fluorophenyl)-5-(trifluoromethyl)pyrrole-3-carbonitrile;

2-(3,5-dichlorophenyl)-5-(trifluoromethyl)-4-(trifluoromethylthio)pyrrole-3-carbonitrile; and 4-bromo-2-(p-chlorophenyl)-5-[($\beta$-bromo-$\beta,\alpha,\alpha$-trifluoro)-ethylthio]pyrrole-3-carbonitrile.

* * * * *